(12) United States Patent
Diao et al.

(10) Patent No.: US 10,245,181 B2
(45) Date of Patent: Apr. 2, 2019

(54) GRIN FIBER MULTI-SPOT LASER PROBE

(71) Applicant: Alcon Research, Ltd., Fort Worth, TX (US)

(72) Inventors: Chenguang Diao, Irvine, CA (US); Ronald T. Smith, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 1284 days.

(21) Appl. No.: 13/723,600

(22) Filed: Dec. 21, 2012

(65) Prior Publication Data

US 2014/0180264 A1    Jun. 26, 2014

(51) Int. Cl.
*A61F 9/008* (2006.01)

(52) U.S. Cl.
CPC ...... *A61F 9/00821* (2013.01); *A61F 9/00823* (2013.01); *A61F 2009/00863* (2013.01); *Y10T 29/49826* (2015.01)

(58) Field of Classification Search
CPC .. A61F 9/00821; A61F 9/008; A61F 9/00804; A61F 2009/00872; A61F 2009/00887; A61F 2009/0087; A61N 5/062
USPC ............... 607/88–94; 606/4–6; 385/123–126
See application file for complete search history.

(56) References Cited

U.S. PATENT DOCUMENTS

| 3,584,948 A | 6/1971 | Herriott |
| 4,062,043 A | 12/1977 | Zeidler et al. |
| 4,111,524 A | 9/1978 | Tomlinson, III |
| 4,274,706 A | 6/1981 | Tangonan |
| 4,679,901 A | 7/1987 | Dammann et al. |
| 4,701,011 A * | 10/1987 | Emkey ............... G02B 6/4203 385/28 |
| 4,865,029 A | 9/1989 | Pankratov et al. |
| 4,919,506 A | 4/1990 | Covey |

(Continued)

FOREIGN PATENT DOCUMENTS

| EP | 1191359 | 3/2002 |
| JP | 2000-50043 | 1/2000 |

(Continued)

OTHER PUBLICATIONS

Definition of Interface. Merriam-Webster Dictionary, retrieved on Feburary 22, 2017; Retrieved from the internet: <http://www.merriam-webster.com/dictionary/interface>.*

(Continued)

*Primary Examiner* — Gary Jackson
*Assistant Examiner* — Sebastian X Lukjan

(57) ABSTRACT

A surgical probe includes a cannula assembly, having a graded index (GRIN) fiber that is configured to receive a multi-spot light beam at a proximal end and to emit the multi-spot light beam at a distal end; an adapter, having a distal end, configured to receive the cannula assembly, with the proximal end of the GRIN fiber, a proximal end, configured to couple to a light guide via a connector and to receive a light delivered by the light guide from a laser source to the adapter, and an interface, configured to couple the light delivered by the light guide to the proximal end of the GRIN fiber; wherein a length of the GRIN fiber is sufficiently long that the interface is outside a patient's eye during a photocoagulation procedure.

18 Claims, 5 Drawing Sheets

(56) References Cited

U.S. PATENT DOCUMENTS

| | | | |
|---|---|---|---|
| 4,985,027 A * | 1/1991 | Dressel | A61B 18/22 606/15 |
| 4,986,262 A | 1/1991 | Saito | |
| 5,090,400 A | 2/1992 | Saito | |
| 5,125,922 A | 6/1992 | Dwyer et al. | |
| 5,150,254 A | 9/1992 | Saitou | |
| 5,261,904 A | 11/1993 | Baker et al. | |
| 5,275,593 A | 1/1994 | Easley et al. | |
| 5,356,407 A | 10/1994 | Easley et al. | |
| 5,370,643 A * | 12/1994 | Krivoshlykov | A61B 18/22 385/117 |
| 5,373,526 A | 12/1994 | Lam et al. | |
| 5,396,571 A | 3/1995 | Saadatmanesh et al. | |
| 5,409,137 A | 4/1995 | Bonomelli | |
| 5,555,129 A | 9/1996 | Konno et al. | |
| 5,630,809 A | 5/1997 | Connor | |
| 5,659,642 A | 8/1997 | King et al. | |
| 5,715,089 A | 2/1998 | Shiraishi | |
| 5,738,676 A * | 4/1998 | Hammer | A61F 9/008 606/17 |
| 5,841,912 A | 11/1998 | Mueller-Fiedler et al. | |
| 5,921,981 A | 7/1999 | Bahmanyar et al. | |
| 5,973,779 A | 10/1999 | Ansari et al. | |
| 5,980,454 A | 11/1999 | Broome | |
| 6,056,128 A | 5/2000 | Bahmanyar et al. | |
| 6,066,128 A | 5/2000 | Bahmanyar et al. | |
| 6,071,748 A | 6/2000 | Modlin et al. | |
| 6,080,143 A | 6/2000 | Connor | |
| 6,096,028 A | 8/2000 | Bahmanyar et al. | |
| 6,097,025 A | 8/2000 | Modlin et al. | |
| 6,241,721 B1 | 6/2001 | Cozean et al. | |
| 6,370,422 B1 | 4/2002 | Richards-Kortum et al. | |
| 6,421,179 B1 | 7/2002 | Gutin et al. | |
| 6,441,934 B1 | 8/2002 | Boord et al. | |
| 6,520,956 B1 | 2/2003 | Huang | |
| 6,539,132 B2 | 3/2003 | Ivtsenkov et al. | |
| 6,562,466 B2 | 5/2003 | Jiang et al. | |
| 6,563,982 B1 | 5/2003 | Xie et al. | |
| 6,572,609 B1 * | 6/2003 | Farr et al. | 606/15 |
| 6,687,010 B1 | 2/2004 | Horii et al. | |
| 6,975,898 B2 | 12/2005 | Seibel | |
| 7,071,460 B2 | 7/2006 | Rush | |
| 7,231,243 B2 | 6/2007 | Tearney et al. | |
| 7,252,662 B2 | 8/2007 | McArdle et al. | |
| 7,566,173 B2 | 7/2009 | Auld et al. | |
| 2001/0055462 A1 | 12/2001 | Seibel | |
| 2002/0013572 A1 | 1/2002 | Berlin | |
| 2002/0054725 A1 | 5/2002 | Ivtsenkov et al. | |
| 2002/0111608 A1 | 8/2002 | Baerveldt et al. | |
| 2002/0165595 A1 * | 11/2002 | Haan et al. | 607/89 |
| 2003/0020922 A1 | 1/2003 | Crowley et al. | |
| 2003/0068133 A1 | 4/2003 | Tatah | |
| 2003/0081220 A1 | 5/2003 | Ostrovsky et al. | |
| 2004/0012856 A1 | 1/2004 | Gutin | |
| 2004/0109164 A1 | 6/2004 | Horii et al. | |
| 2004/0116909 A1 | 6/2004 | Neuberger et al. | |
| 2004/0195511 A1 | 10/2004 | Elmore et al. | |
| 2005/0033389 A1 * | 2/2005 | Auld | A61B 18/22 607/89 |
| 2005/0075704 A1 | 4/2005 | Tu et al. | |
| 2005/0140033 A1 | 6/2005 | Jiang et al. | |
| 2005/0143719 A1 | 6/2005 | Sink | |
| 2005/0154379 A1 | 7/2005 | McGowan, Sr. et al. | |
| 2005/0197655 A1 | 9/2005 | Telfair et al. | |
| 2005/0220401 A1 | 10/2005 | Jiang et al. | |
| 2005/0240168 A1 | 10/2005 | Neuberger et al. | |
| 2005/0245916 A1 | 11/2005 | Connor | |
| 2006/0013533 A1 | 1/2006 | Slatkine | |
| 2006/0100613 A1 | 5/2006 | McArdle et al. | |
| 2006/0106370 A1 | 5/2006 | Baerveldt et al. | |
| 2006/0114473 A1 | 6/2006 | Tearney et al. | |
| 2006/0195076 A1 | 8/2006 | Blumenkranz et al. | |
| 2007/0027443 A1 * | 2/2007 | Rose | A61C 1/088 606/16 |
| 2007/0057211 A1 | 3/2007 | Bahlman et al. | |
| 2007/0121069 A1 | 5/2007 | Andersen et al. | |
| 2007/0142881 A1 * | 6/2007 | Hennings | 607/89 |
| 2007/0179430 A1 | 8/2007 | Smith et al. | |
| 2007/0238955 A1 | 10/2007 | Tearney et al. | |
| 2007/0265602 A1 | 11/2007 | Mordaunt et al. | |
| 2007/0296094 A1 | 12/2007 | Jiang et al. | |
| 2007/0299430 A1 | 12/2007 | McArdle et al. | |
| 2008/0013960 A1 | 1/2008 | Tearney et al. | |
| 2008/0025672 A1 * | 1/2008 | Boutoussov | A61B 18/20 385/80 |
| 2008/0097225 A1 | 4/2008 | Tearney et al. | |
| 2008/0246919 A1 | 10/2008 | Smith | |
| 2008/0308730 A1 | 12/2008 | Vizi et al. | |
| 2009/0015923 A1 * | 1/2009 | Auld et al. | 359/566 |
| 2009/0043296 A1 | 2/2009 | Foster et al. | |
| 2009/0075229 A1 * | 3/2009 | Rizoiu | A61C 1/0046 433/29 |
| 2010/0027943 A1 | 2/2010 | Armani et al. | |
| 2010/0137852 A1 * | 6/2010 | Boutoussov | A61B 18/20 606/18 |
| 2011/0038174 A1 | 2/2011 | Papac et al. | |
| 2011/0122366 A1 * | 5/2011 | Smith | A61B 1/313 351/221 |
| 2011/0144627 A1 * | 6/2011 | Smith | A61F 9/008 606/4 |
| 2011/0319874 A1 * | 12/2011 | Mintz | A61F 9/00802 606/4 |
| 2012/0022510 A1 * | 1/2012 | Welches et al. | 606/3 |
| 2013/0038836 A1 | 2/2013 | Smith | |

FOREIGN PATENT DOCUMENTS

| | | |
|---|---|---|
| JP | 2002-286920 | 10/2002 |
| JP | 2008-526384 | 7/2008 |
| WO | 97/017011 | 5/1997 |
| WO | 99/08612 | 2/1999 |
| WO | 2006/074469 | 7/2006 |
| WO | 2006/116141 | 11/2006 |
| WO | WO 2011/102870 | 8/2011 |

OTHER PUBLICATIONS

International Search Report and Written Opinion issued for PCT/US2013/075925 dated Apr. 18, 2014, 8 pgs.

Extended European Search Report issued for European Patent Application No. 13865679.8 dated Jul. 11, 2016, 5 pgs.

* cited by examiner

GRIN FIBER MULTI-SPOT LASER PROBE

BACKGROUND

Technical Field

This application relates to a laser probe for use in ophthalmic procedures and more particularly to a multi-spot laser probe for use in photocoagulation therapy.

Description of Related Art

State-of-the-art laser photocoagulation therapies have been used for some time to deliver a multi-spot laser beam to retinal tissue. Multi-spot laser beams enhance the areal coverage of the therapy, increasing the speed and reducing the invasiveness of the technique. Some attempts to create a multi-spot laser probe have used a fiber bundle including a plurality of fibers. The fiber bundle is coupled to the laser source in the proximal end of the probe and delivers the laser light from multiple fibers at the distal end of the probe. One problem that arises with fiber bundle probes is that the telecentric laser beam transmitted to the tissue from the distal end of the multiple fibers should be directed into different angular directions to distribute the resulting laser beam spots on a wide area of the retina. To provide such wide area distribution, multi-spot/multi-fiber laser probes have been developed having the distal ends of the fibers bent into the desired angular directions. However, such bending is cumbersome, increases costs, and also increases the probe diameter at the distal end, which undesirably increases invasiveness.

Some attempts to cure the problem of distribution of laser spots in the retinal tissue involve the use of a GRIN lens at a distal point or end of the probe. For example, a fiber bundle may be coupled to a GRIN lens at the distal end, so that the multi-spot pattern can be projected onto the retina at the desired distance and magnification. However, this approach has various problems.

One problem is that using the GRIN lens introduces a thermal management challenge at the distal end of the probe. Indeed, even a slight coupling inefficiency between the fiber bundle and the GRIN lens generates an undesirable amount of heat trapped at the interface that is difficult to remove. The distal end of the probe typically has reduced dimensions to reduce invasiveness. Thus, heat generated at the distal end is accumulated there, since the heat conductive elements in the probe have too small dimensions to conduct all the heat away. Accordingly, the fiber-GRIN lens interface is sometimes referred to as a hotspot. As the temperature of the probe tip raises, optical elements within the tip, including the GRIN lens, may become misaligned or loosen.

Another problem is that the overheating-related malfunction takes place inside the eye, multiplying the associated risk factors. As an example, the GRIN lens and other elements may become loose, thus creating the risk of falling inside the eye, a highly undesirable outcome.

A third drawback of the existing GRIN lens designs is that the whole probe, which includes the GRIN lens, the fiber bundle, the cannula with a customized adapter, the handpiece and the fiber connectors all belong to a disposable, discarded after each procedure. Each procedure requiring new disposables raises the total cost of the procedures and thus reduces the availability of the procedure.

Accordingly, there is a need for improved multi-spot laser probes that are thermally robust and reduce the risk of damaging the tissue by heat or loose components. There is also the need for a probe composed of mostly reusable components, with only a small portion disposable.

SUMMARY

In order to address the above discussed problems, a surgical probe, according to embodiments of the present invention can include a cannula assembly, having a graded index (GRIN) fiber, configured to receive a multi spot beam at a proximal end and to emit the multi-spot light beam at a distal end; an adapter, having a distal end, configured to receive the cannula assembly with the proximal end of the GRIN fiber, a proximal end, configured to couple to a light guide via a connector and to receive a light delivered by the light guide from a laser source to the adapter, and an interface, configured to couple the light delivered by the light guide to the proximal end of the GRIN fiber; wherein a length of the GRIN fiber is sufficiently long that the interface is outside a patient's eye during a photocoagulation procedure.

In related embodiments, a method to fabricate a surgical probe can include encasing a graded index (GRIN) fiber into a cannula system, the GRIN fiber configured to receive a multi-spot light beam at a proximal end and to emit the multi-spot light beam at a distal end; coupling the cannula system, with the proximal end of the GRIN fiber, to a distal end of an adapter; and coupling a light guide via a connector to a proximal end of the adapter, the light guide configured to deliver light from a laser source to the adapter; wherein the adapter comprises an interface, configured to couple the light delivered by the light guide to the proximal end of the GRIN fiber; and a length of the GRIN fiber is sufficiently long that the interface is outside a patient's eye during a photocoagulation procedure.

These and other embodiments of the present invention will be described in further detail below with reference to the following drawings.

BRIEF DESCRIPTION OF THE DRAWINGS

In the figures, elements having the same reference number have the same or similar functions.

DETAILED DESCRIPTION

Laser photocoagulation therapy addresses ocular conditions such as retinal detachments and tears as well as proliferative retinopathy resulting from diseases such as diabetes. The abnormally high blood sugar in a diabetic patient stimulates retinal vessels to release growth factors that in turn encourage an undesirable proliferation of blood vessels and capillaries over the retinal surface. These proliferated blood vessels are delicate and will readily bleed into the vitreous humor. The body responds to the damaged vessels by producing scar tissue, which may then cause the retina to detach and eventually cause blindness.

Figure 1:
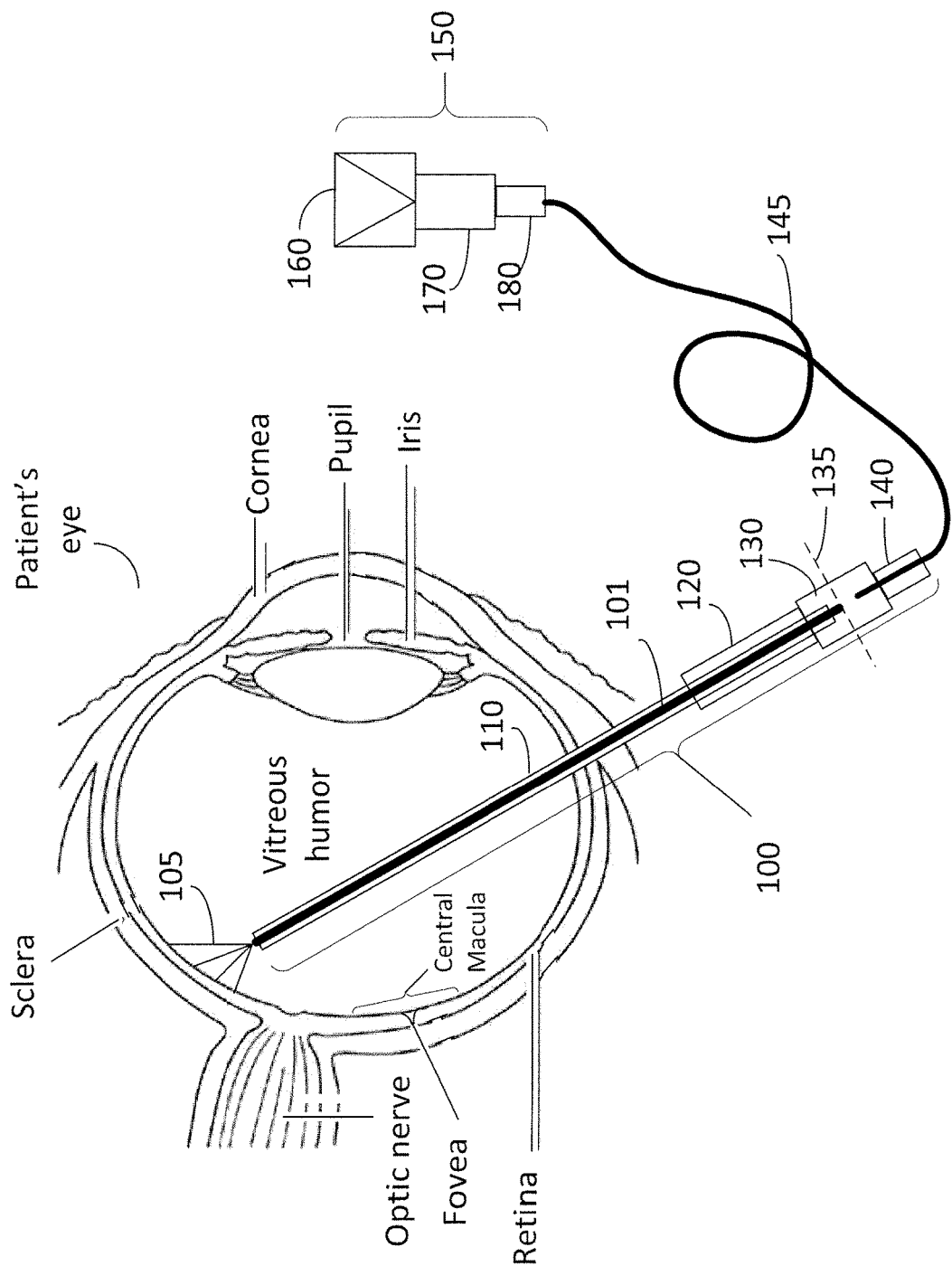
FIG. 1 shows a surgical probe adapted for producing a multi-spot laser beam for retinal photocoagulation procedures, according to some embodiments.

FIG. 1 shows a surgical probe 100 adapted for producing a multi-spot laser beam 105 for retinal photocoagulation procedures emitted from a gradient index (GRIN) fiber 101 according to some embodiments. Probe 100 can be inserted in the patient's eye through an incision and illuminates a portion of the retina with beam 105. Probe 100 may include a cannula 110 to accommodate and support the GRIN fiber 101, a handling piece or handpiece 120 to house the cannula 110, and an adapter 130 that can couple to a connector 140. Cannula 110 can be removably docked into a distal end of the adapter 130, and connector 140 can be docked into a proximal end of the adapter 130. This design allows a proximal end of the GRIN fiber 101 to receive a light beam or multiple beam-components from connector 140 at an interface 135 within adapter 130 and thus outside the patient's eye during the photocoagulation procedure.

Surgical probe 100 receives the light beam through connector 140 guided by an optical cable 145, which is coupled to a laser source 150. Optical cable 145 may include an optical fiber bundle, guiding the beam-components, or a single optical fiber. According to some embodiments, laser source 150 may include a laser device 160, a coupler 170, which may include a beam splitter and a lens, and a connector 180.

According to FIG. 1, in embodiments described hereinafter a 'proximal' element or portion refers to an element or portion that is closer to laser source 150. Likewise, a 'distal' element or portion refers to an element or portion that is closer to the patient's eye. Thus, for example, multi-spot beam 105 is in a distal position relative to surgical probe 100. And optical cable 145 is in a proximal position relative to surgical probe 100.

As discussed above, probe 100 faces considerable heal production at the interface or hotspot of the GRIN fiber 135 and the laser connector 140 even for very small optical mismatches, leading to at least the three described problems. In contrast to existing systems that use a small and short GRIN lens at the tip of the probe 100 and therefore have the hotspot 135 at the distal tip of the probe 100, deep inside the eye, in the present embodiments GRIN fiber is long enough so that hotspot 135 can be outside the patient's eye. This design offers improvements for all three above described problems.

(a) Some probes 100 dissipate the heat produced at the interface 135 in an improved manner. Indeed, outside of the patient's eye, the mass and dimensions of adapter 130 surrounding interface 135 may be increased, as well as heat-exchange structures can be coupled to cannula 110, such as large surface metal structures or cooling ribs made with high thermal conductivity materials. By increasing the mass, size and surface of adapter 130, heat generated at interface 135 may be dissipated outside the eye in an efficient manner.

For example, adapter 130 may include a material with a high thermal-conductivity, such as a metal. This improves the thermal performance of adapter 130. Also, the more robust thermal performance in embodiments consistent with the present disclosure increases manufacturing yield after sterilization and environmental testing procedures. This is to be compared to probes that dissipate the heat inside the eye that is extracted only through the cannula that is a poor heat conductor because of its small size, possibly leading to over-heating-related damage in the biological tissue.

Also, some embodiments may include a thermally conductive adhesive between GRIN fiber 101 and cannula 110, to help dissipate heat produced at interface or hotspot 135. Further, cannula 110 may be made of a high thermal conductivity material, such as a metal, for example copper, to enhance the thermal robustness of the assembly.

(b) The mechanical robustness of the surgical probe 100 according to embodiments disclosed herein is also enhanced by the long contact area between GRIN fiber 101 and cannula 110, extended along the entire length of the GIN fiber 101. Thus, the attachment of GRIN fiber 101 and cannula 110 is stronger, reducing dramatically the risk of major failure, including the dislodging of GRIN fiber 101 from the cannula 110.

Even if a material failure occurs at hotspot 135 due to thermal stress or mechanical stress, the risk that any of the components may become trapped inside the patient's eye is limited, increasing operational safety. Increasing operational safety is highly desirable for the manufacturer of surgical probe 100, due to the reduced liability.

(c) Finally, in embodiments, the disposable portion of the probe 100 can be only the cannula 110 that contains the GRIN fiber 101 and the handpiece 120. This disposable can be docked into adapter 130. Adapter 130 requires precise engineering to enable a precise optical coupling between GRIN fiber 101 and laser guide 145. Thus, disposables that include adapter 130, and possibly connector 140, laser guide 145, and connector 180 are more expensive, inflating the price and thus limiting the accessibility of the procedure as they are to be discarded or disposed after every procedure. For this reason, disposables that can be designed not to include adapter 130, connector 140, laser guide 145, and connector 180 are considerably cheaper, making the procedure accessible to a wider segment of the population.

In laser photocoagulation procedures using a surgical probe as in embodiments disclosed herein, surgical probe 100 is used to cauterize blood vessels at various laser burn spots across the retina. Because the laser may damage vision cells such as rods and cones that are present in the retina, eyesight may be affected through the therapy. As shown in FIG. 1, since vision is most acute at the central macula of the retina, the surgeon can direct the beam 105 to peripheral areas of the retina to effect the photocoagulation, sacrificing some peripheral vision to preserve or restore central vision.

During the procedure, the surgeon may first couple into probe 100 a non-burning, aiming beam such that the retinal area to be photocoagulated is marked and illuminated. Due to the availability of low-power red laser diodes, the aiming beam is generally a low-power red laser light. Pointing this aiming beam allows the surgeon to position and direct probe 100 accurately to the targeted portion of the retina. Once the surgeon has positioned and directed surgical probe 100, the surgeon can activate laser source 150 through a foot pedal or like mechanism, to then photocoagulate the illuminated area, sometimes referred to as "to burn" or "to fire".

Having burned a retinal spot, the surgeon repositions probe 100 to illuminate a new spot with multi-spot beam 105, activates laser source 150, redirects surgical probe 100, and so on. The procedure is repeated until a suitable array of burned laser spots are distributed across the retina. The number of required laser photocoagulation spots for a typical treatment of the retina may be about 1,000 to 1,500 spots. Systems that break up the initial laser beam into 2, 4, or 6 beam components e.g. by refracting the beam by faceted optical elements can burn 2, 4, or 6 spots simultaneously, thus reducing the number of required laser activations, or "firings" by a factor of 2, 4, or 6, the number of beam-components. Thus, using a multi-spot beam 105 can increase the speed of the photocoagulation procedure dramatically.

Embodiments of a surgical probe 100 may include a "multi-spot/multi-fiber" laser probe, producing multiple laser beams through a corresponding array of optical fibers. For example, optical cable 145 may include a fiber bundle having a plurality of optical fibers, each fiber carrying a portion of the illumination light, or beam component from laser source 150 to surgical probe 100. In such embodiments, coupler 170 can include an adaptor and optical elements to efficiently couple light from laser 160 into the fiber bundle in optical cable 145. In some embodiments, coupler 170 may include optical elements such as a graded index (GRIN) lens, a diffractive beam splitter, or a faceted optical element. In some embodiments, coupler 170 may include a combination of a GRIN lens and a diffractive beam splitter, and other optical elements such as a lens. Accordingly, coupler 170 may be designed so as to receive a standard optical cable connector 180.

In some embodiments, surgical probe 100 may be adapted to use a single optical fiber in optical cable 145. Such embodiments are denoted herein as a "multi-spot/single-fiber" laser probe. In a multi-spot/single fiber configuration adapter 130 in surgical probe 100 may include optical elements to efficiently couple the laser light from a single optical fiber to the GRIN fiber 101 that can efficiently deliver and emit the beam components at its distal end to illuminate multiple spots.

Regardless of whether a surgical probe 100 is a single-fiber probe or a multi-fiber probe, it can be compatible with connector 140 used to connect probe 100 and its adapter 130 to the laser source 150. In this regard, it is conventional for optical cable 145 coupled to laser source 150 to have a standardized interconnect such as a subminiature version A (SMA) interconnect. For example, laser source 150 may have a female SMA connector in coupler 170 that receives connector 180 from optical cable 145. Connector 180 in optical cable 145 may be a standard ST connector. For a conventional single-spot/single-fiber laser probe, a male SMA connector 180 may incorporate a single fiber in optical cable 145. In some embodiments, connector 180 may include a proximal end of optical cable 145 cut at an angle relative to the longitudinal axis of the optical cable. This may reduce undesirable feedback from optical cable 145 to laser source 150.

Laser source 150 can provide a focused beam to the male SMA connector 180 with a beam waist with a much smaller diameter than a diameter of the single fiber used in optical cable 145. For example, the laser beam waist may be 5 µm, or less, while the diameter of a single fiber in optical cable 145 may be 75 µm, or more. In some embodiments, the diameter of the laser beam waist may be 2 µm, 1 µm, or less, while a single fiber may have a diameter of about 10 µm, or more. Thus, a multi-spot/single fiber surgical probe 100 with a narrow beam waist can couple the laser source 150 efficiently to the optical probe 100.

One of ordinary skill in the art of fiber optic technology will recognize that embodiments of the present disclosure are not limiting with respect to the type of optical fiber used in optical cable 145. For example, some embodiments may use a fiber bundle including a plurality of multimode optical fibers. In some embodiments, the fiber bundle may include a plurality or at least one single mode optical fiber. Even in multi-spot/single fiber embodiments, the single fiber used may be either a multimode optical fiber or a single mode optical fiber.

According to some embodiments, GRIN fiber 101 may be designed to relay a multi-spot image from interface or hotspot 135 outside the eye onto the retina via multi-spot beam 105. GRIN fiber 101 may include a cylindrical core having a refractive index that varies radially. GRIN fiber 101 can act like a series of relay lenses, configured to receive the multi spot light beam at a proximal end and to relay it to a first image plane, then relay this image to a second image plane, and so on, until the multi-spot pattern is relayed to the distal end of the GRIN fiber, where it is emitted towards the eventual target.

To reduce heat dissipation, a proximal end face of GRIN fiber 101 at interface 135 may be coated with an anti-reflection (AR) layer at the wavelength of the laser source. The proximal end face of GRIN fiber 101 may also be cut at an angle relative to the axis of symmetry of GRIN fiber 101, to avoid undesirable feedback to laser source 150.

In embodiments of surgical probe 100 as disclosed herein, cannula 110 with GRIN fiber 101 and housing or handpiece 120 may be disposable. Thus, a surgeon may retain adapter 130 of surgical probe 100 together with laser source 150 and optical cable 145 after individual procedures and dispose only the disposable cannula 110 and handpiece 120. Further, according to some embodiments, surgical probe 100 can be adapted to accept or dock optical cable 145 including either a fiber bundle or a single fiber. This will be described in more detail below, in relation to FIGS. 2A-B.

Figure 2A:
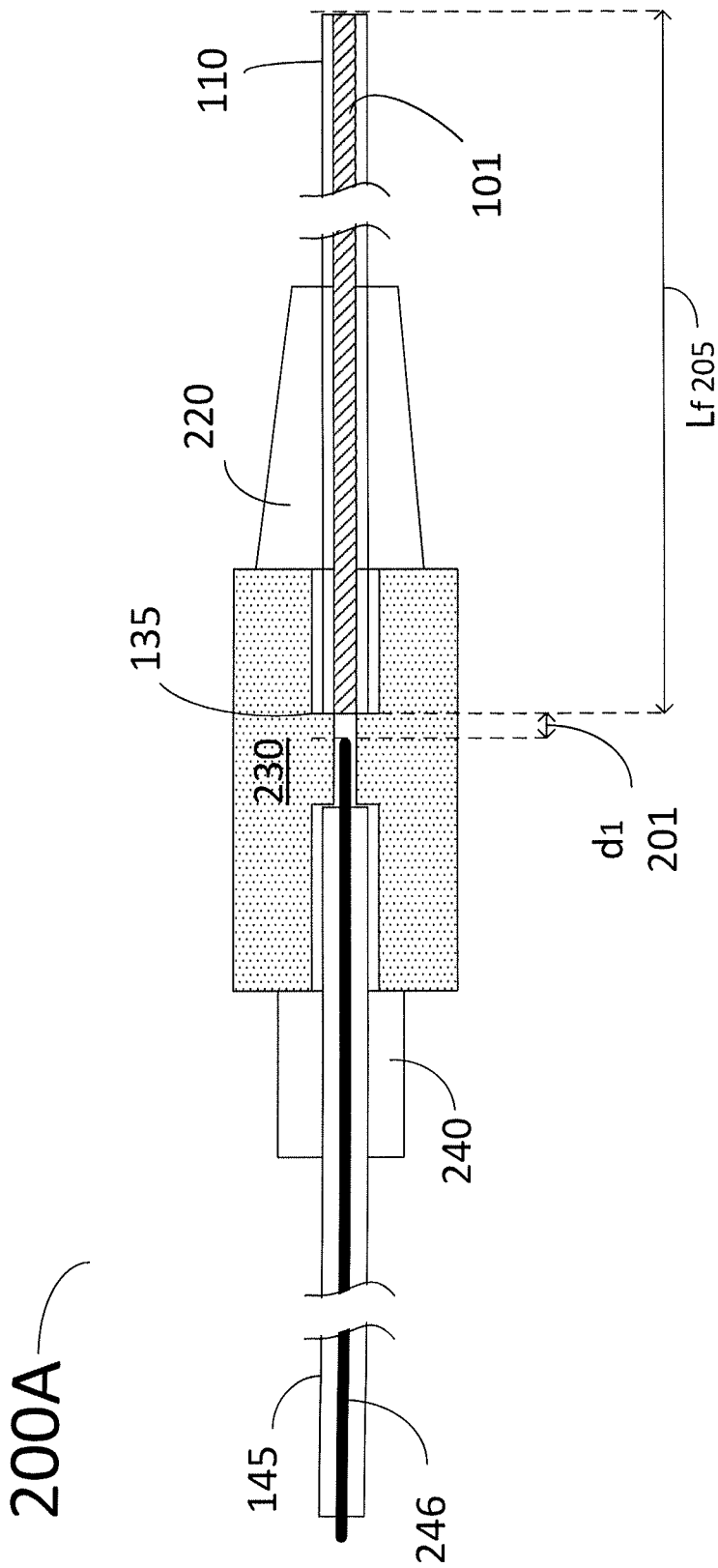
FIG. 2A shows a longitudinal cross-sectional view of a surgical probe, according to some embodiments.

FIG. 2A shows a longitudinal cross-sectional view of a surgical probe 200A that can be an embodiment of surgical probe 100. Surgical probe 200A can include adapter, or mounting piece, 230 configured to couple GRIN fiber 101 to optical cable 145. In some embodiments, optical cable 145 can include a fiber bundle 246 having a plurality of optical fibers. Surgical probe 200A can also include handling piece 220, which can secure or dock cannula 110 into adapter or mounting piece 230. Further, handling piece or handpiece 220 may be adapted for being manipulated either manually by a surgeon or by a machine, such as a surgical robot having an arm adapted to grab surgical probe 200A at handling piece 220. GRIN fiber 101 may have a total length Lf 205 which may be in the range of 10-300 mm or 30-100 mm. In some embodiments, GRIN fiber 101 can be 200 to 500 microns in diameter and composed of $SiO_2$ and $GeO_2$, with a parabolic refractive index profile.

As illustrated in FIG. 2A, a proximal end of GRIN fiber 101 can reach inside adapter 230, ending at interface 135. Likewise, fiber bundle 246 can reach inside adapter 230 so that a pre-selected distance d1 201 is formed between fiber bundle 246 and GRIN fiber 101.

Figure 2B:
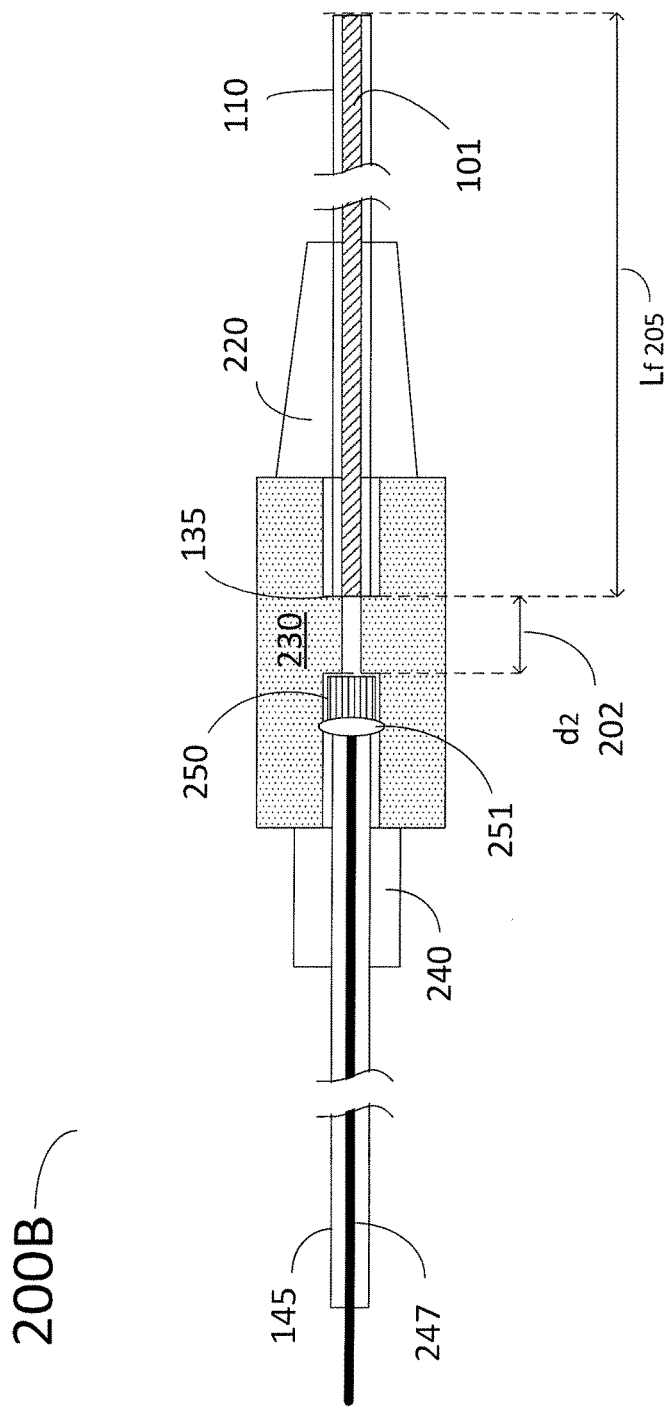
FIG. 2B shows a longitudinal cross-sectional view of a surgical probe, according to some embodiments.

FIG. 2B shows a longitudinal cross-sectional view of a surgical probe 200B, according to some embodiments. Surgical probe 200B includes adapter 230 configured to couple GRIN fiber 101 to optical cable 145. In some embodiments, optical cable 145 includes a single fiber 247 and a diffractive beam splitter 250. In some embodiments, single fiber 247 may be coupled to diffractive beam splitter 250 via a lens 251. Lens 251 collects laser light from single fiber 247, passes the laser light through diffractive beam splitter 250, and projects a number of beam-components onto the proximal face of GRIN fiber 101. In some embodiments, diffractive beam splitter 250 and lens 251 can be part of an extended interface 135.

As illustrated in FIG. 2B, a proximal end of GRIN fiber 101 can reach inside adapter 230 up to interface 135. Likewise, fiber 247 can reach inside adapter 230 so that a pre-selected distance d2 202 is formed between diffractive beam splitter 250 and GRIN fiber 101.

Figure 3:
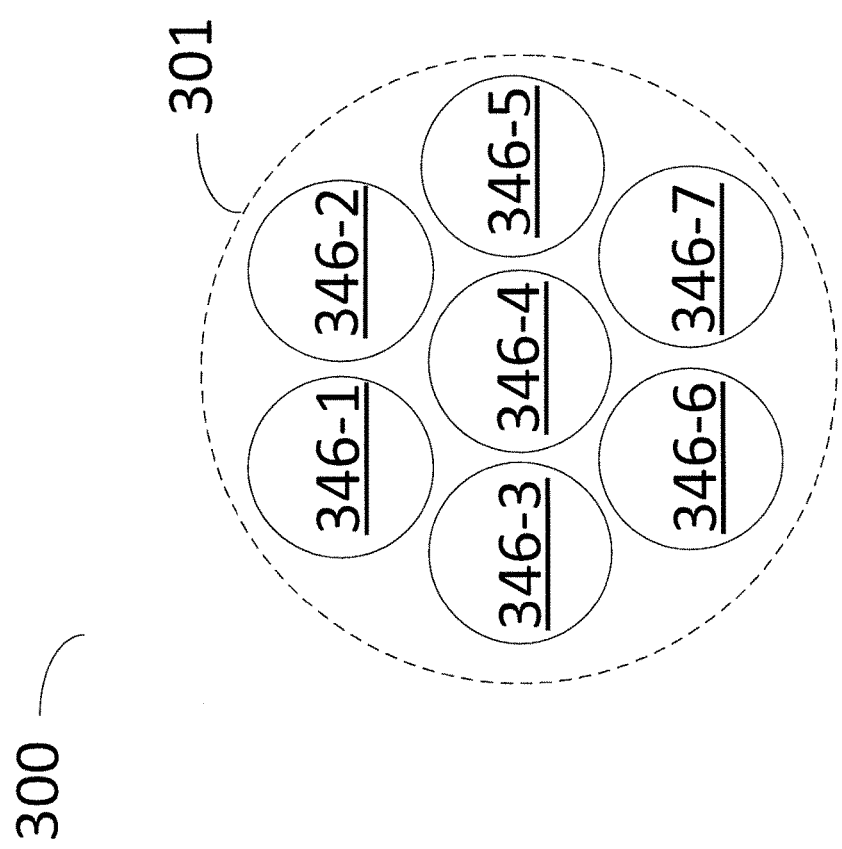
FIG. 3 shows a radial cross-sectional view of a multi-spot configuration within the proximal end of a surgical probe, according to some embodiments.

FIG. 3 shows a radial cross-sectional view of a multi-spot plane 300 within the proximal end of a surgical probe, according to some embodiments. Configuration 300 includes laser spots 346-1, 346-2, 346-3, 346-4, 346-5, 346-6, and 346-7 collectively referred hereinafter as laser spots 346. Configuration 300 also includes a perimeter 301 of the cross-section in a GRIN fiber 101, which encircles light spots 346. Accordingly, light spots 346 may form an image plane on the proximal surface of GRIN fiber 101, abutted to interface 135 (cf. FIGS. 2A-B). In some embodiments, light spots 346 may be projected on to the proximal surface of GRIN fiber 101 by a fiber bundle, such as fiber bundle 246 (cf. FIG. 2A). In some embodiments, light spots 346 may be the image plane of a diffraction beam splitter such as diffraction beam-splitter 250 coupled to a lens 251 (cf. FIG. 2B).

FIG. 3 shows six light spots 346 oriented in a hexagonal geometry ('honeycomb'). One of ordinary skill would recognize that there is nothing limiting as to the exact geometry and number of light spots 346 in configuration 300. In embodiments where light spots 346 correspond to fiber bundle 246, a central fiber 346-4 may be circumferentially surrounded by six outer fibers 346-1, 346-2, 346-3, 346-5, 346-6, and 346-7. In some embodiments, each fiber in the fiber bundle may have a numerical aperture (NA) in the range of 0.2-0.3, such as 0.22, achieved through a 75 µm glass core encased in a 90 µm cladding surrounded by a 101 µm jacket. To minimize the amount of uncoupled laser energy, GRIN fiber 101 may have a diameter sufficient to encompass all of the fibers, as shown in FIG. 3.

In embodiments where fiber bundle 246 and GRIN fiber 101 are axi-symmetric, clocking or 'roll' alignment between fiber bundle 246 and GRIN fiber 101 may not be necessary. In some embodiments, a distal end of fiber bundle 246 and a proximal end of GRIN fiber 101 may have an angle to reduce interface reflections, optical feedback and interference. In such embodiments it may be desirable to include a clocking notch in adapter 230, so that the orientation of the distal end of fiber bundle 246 and the proximal end of GRIN fiber 101 align with each other.

In that regard, whereas the distribution of light spots in plane 300 shown in FIG. 3 is axially symmetric, other configurations are possible, as one of ordinary skill in the art may recognize. For example, fibers in fiber bundle 246 may be arranged in any suitable distribution. Also, in some embodiments a suitable diffractive beam splitter 250 may be used to generate any desirable pattern of light spots 346. For example, the array of light spots 346 may form a line in plane 300. In some embodiments, the array of light spots 346 may form an ellipse in plane 300, having an eccentricity that may be desirably adjusted. For example, some embodiments may combine lens 251, which may be a cylindrical lens, with diffractive beam splitter 250 to form an elliptical pattern of laser spots in plane 300. Lens 251 may also be a convex lens having two different focal lengths along perpendicular planes, to generate an elliptical pattern of light spots in plane 300.

In some embodiments, the probe 100 can be optically coupled to a surgical light system, comprising the light or laser source 150, configured to provide light for the light guide or optical cable 145, and a control processor, configured to control an operation of the surgical light system.

Figure 4:
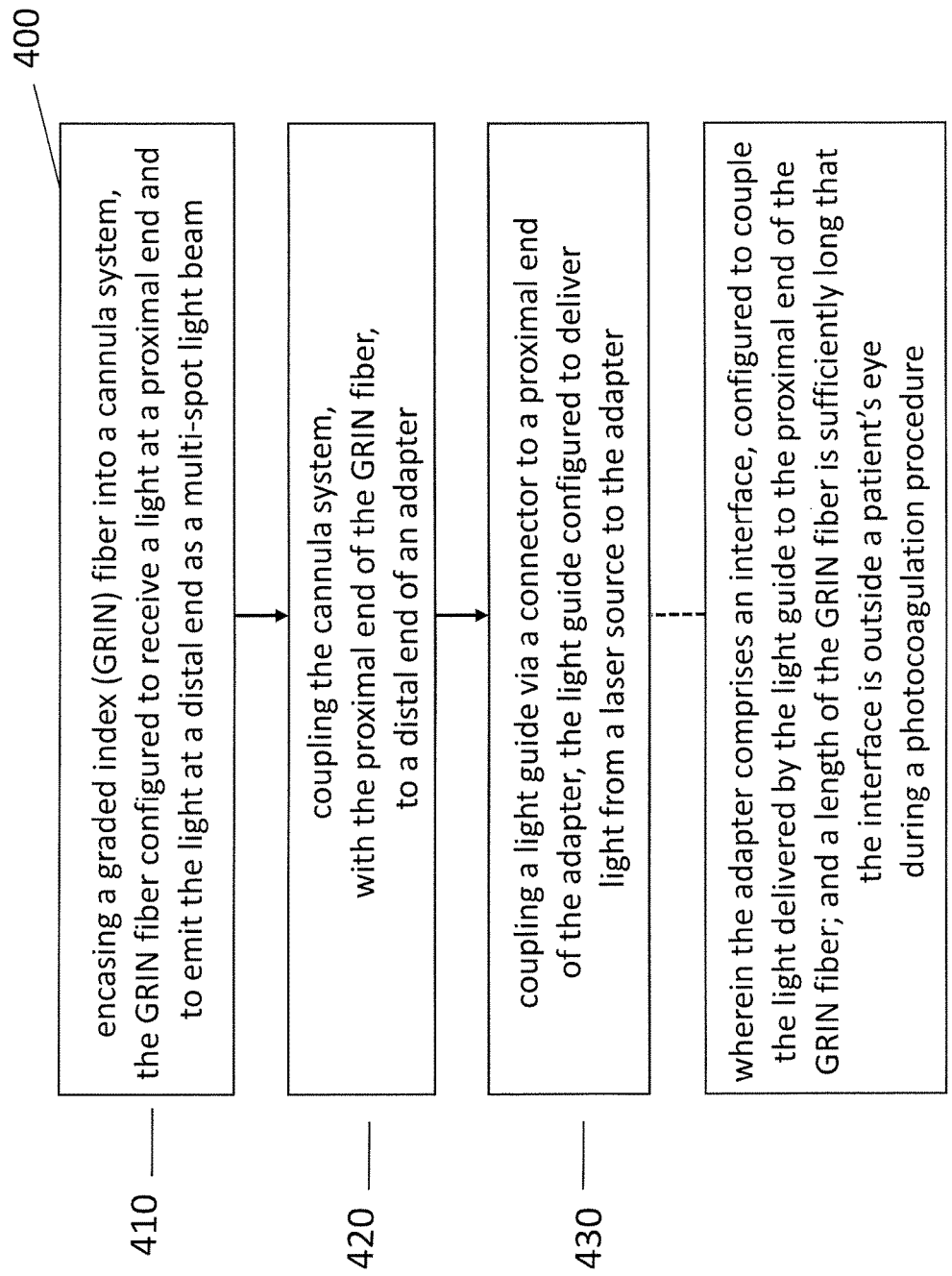
FIG. 4 shows a flow chart of a method for creating a multi-spot surgical probe, according to some embodiments.

FIG. 4 shows a flow chart of a method 400 for fabricating a multi-spot surgical probe, according to some embodiments. Method 400 can comprise:

step 410: encasing a graded index (GRIN) fiber into a cannula system, the GRIN fiber configured to receive a multi-spot light beam at a proximal end and to emit the multi-spot light beam at a distal end;

step 420: coupling the cannula system, with the proximal end of the GRIN fiber, to a distal end of an adapter; and step 430: coupling a light guide via a connector to a proximal end of the adapter, the light guide configured to deliver light from a laser source to the adapter; wherein the adapter comprises an interface, configured to couple the light delivered by the light guide to the proximal end of the GRIN fiber; and a length of the GRIN fiber is sufficiently long that the interface is outside a patient's eye during a photocoagulation procedure.

In some embodiments, the GRIN fiber can be GRIN fiber 101, the cannula assembly can be cannula assembly 110, the adapter can be adapter 130, the interface can be interface 135, the connector can be connector 140, and the light guide can be light guide 145.

In some embodiments, the light guide can include a fiber bundle to the proximal end of the adapter. In other embodiments, the light guide can include a single optical fiber, to be coupled to the proximal end of the adapter, wherein the adapter comprises at the interface a lens optically coupled to the optical fiber; and a diffractive beam splitter optically coupled to the lens. In some cases, a length of the GRIN fiber can be in the range of 30-100 mm. In some embodiments, the cannula assembly can include a cannula, configured to encase the GRIN fiber and a handpiece, configured for coupling the cannula to the adapter, providing a heat exchange system, or being manipulated by a surgeon or a surgical machine.

In a related method 400', a step 410' can include providing an adapter with a proximal end and a distal end. The adapter in step 410' may be adapter 130 as described in relation to FIGS. 1-2 above.

Step 420' can include configuring the proximal end of the adapter to receive a connector. The connector in step 420' may be a fiber connector, such as connector 140 in FIGS. 1-2. The connector may be configured to couple or dock a light guide into adapter 130. The light guide can be the optical cable 145. Optical cable 145 can be a fiber bundle or a single fiber.

Step 430' can include forming a cannula assembly. For example, the cannula assembly may include a GRIN fiber 101, cannula 110, and handpiece or housing 120, described in relation to FIGS. 1-2. Further, according to some embodiments, step 430' may include fixing the GRIN fiber 101 into the cannula 110 using an adhesive. The adhesive fixing of GRIN fiber 101 to cannula 110 may have a high thermal conductivity.

Step 440' can include configuring the distal end of the adapter to receive a proximal portion of the cannula assembly.

Step 450' can include forming an adapter interface inside the adapter, where the GRIN fiber 101 can receive the light emitted by the light guide 145. The interface can be the interface 135 described earlier. In embodiments where the light guide involves a single fiber, the adapter may include a lens and a diffractive beam splitter, such as lens 251 and diffractive beam splitter 250 in FIG. 2B. The adapter can be configured such that a distance between the distal end of the light guide and the proximal end of the GRIN fiber is selected to minimize the reflection off the GRIN fiber 101. To manage the small fraction of optical power still reflected from GRIN fiber 101, in some embodiments the adapter may be formed of a material having a high thermal conductivity, such as a metal.

According to some embodiments, the GRIN fiber 101 in step 430' may have a length sufficiently long so that an interface where the GRIN fiber 101 receives the light of the light guide in the adapter can be outside a patient's eye during photocoagulation procedure.

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

The invention claimed is:

1. A surgical probe, comprising:
   a cannula assembly, having
   a graded index (GRIN) fiber that is configured to receive a multi-spot light beam at a proximal end and to emit the multi-spot light beam at a distal end, and a cannula encasing the GRIN fiber;
   a handpiece coupled to the cannula assembly with a proximal portion of the GRIN fiber extending into a proximal end of the handpiece, the handpiece configured to be manipulated by a surgeon or a surgical machine to control positioning of the distal end of the GRIN fiber; and
   an adapter, having
   a distal end configured to receive the proximal portion of the handpiece containing the proximal portion of the GRIN fiber,
   a proximal end, configured to couple to a light guide via a connector and to receive a light delivered by the light guide from a laser source to the adapter, and
   an interface configured between the distal end of the adapter and the proximal end of the adapter;
   wherein the interface is outside a patient's eye when the cannula is inserted into the patient's eye during a photocoagulation procedure;
   wherein the proximal end of the GRIN fiber is spaced from a distal end of the light guide by a pre-selected distance inside the adapter thereby coupling the light delivered by the light guide to the proximal end of the GRIN fiber in the adapter;
   wherein the cannula is removably docked to the adapter.

2. The surgical probe of claim 1, the light guide comprising:
   a fiber bundle.

3. The surgical probe of claim 1, wherein:
   the light guide comprises a single optical fiber; and
   the adapter comprises, at the interface,
      a lens, optically coupled to the optical fiber; and
      a diffractive beam splitter, optically coupled to the lens.

4. The surgical probe of claim 1, wherein the handpiece is further configured for providing a heat exchange system.

5. The surgical probe of claim 1, wherein:
   the cannula comprises a high thermal-conductivity metal.

6. The cannula assembly of claim 1, wherein:
   the GRIN fiber is encased into the cannula with a highly heat-conducting adhesive along a length of the GRIN fiber.

7. The surgical probe of claim 1, wherein:
   the cannula assembly is disposable, and
   the adapter is not disposable.

8. The surgical probe of claim 1, wherein:
   the surgical probe is optically coupled to a surgical light system, comprising
      a light source, configured to provide light for the light guide; and
      a control processor, configured to control an operation of the surgical light system.

9. The surgical probe of claim 1, wherein:
   the adapter comprises a heat exchange structure.

10. The surgical probe of claim 1, wherein:
    the GRIN fiber has a diameter between 200 microns and 500 microns.

11. The surgical probe of claim 1, wherein:
    the proximal end of the GRIN fiber is coated with an anti-reflective coating.

12. The surgical probe of claim 1, wherein:
    the proximal end of the GRIN fiber is cut at an angle relative to the axis of symmetry of the GRIN fiber.

13. The surgical probe of claim 1, wherein:
    the GRIN fiber comprises a cylindrical core having a refractive index that varies radially.

14. The surgical probe of claim 1, wherein:
    the handpiece is longitudinally aligned with a proximal portion of the GRIN fiber.

15. The surgical probe of claim 1, wherein:
    the handpiece is adjacent to the adapter.

16. The surgical probe of claim 1, wherein:
    the proximal end of the GRIN fiber is disposed within the adapter.

17. The surgical probe of claim 1, wherein:
    a proximal end of the cannula disposed within the adapter.

18. The surgical probe of claim 1, wherein:
    the proximal end of the GRIN fiber and the distal end of the light guide are aligned along a lumen of the adapter.

* * * * *